US010861600B2

(12) United States Patent
Warner et al.

(10) Patent No.: US 10,861,600 B2
(45) Date of Patent: Dec. 8, 2020

(54) METHOD AND SYSTEM FOR USER-VERIFIABLE CERTIFICATION OF SOFTWARE FOR MEDICAL DEVICES

(71) Applicant: General Electric Company, Schenectady, NY (US)

(72) Inventors: Adrian F. Warner, Wauwatosa, WI (US); Daniel R. Schneidewend, Wauwatosa, WI (US); Nicholas Nekich, Wauwatosa, WI (US); Linda Helvick, Wauwatosa, WI (US); Vivek Sachdev, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 281 days.

(21) Appl. No.: 15/718,267

(22) Filed: Sep. 28, 2017

(65) Prior Publication Data

US 2019/0095587 A1 Mar. 28, 2019

(51) Int. Cl.
*H04L 9/32* (2006.01)
*G16H 40/40* (2018.01)
(Continued)

(52) U.S. Cl.
CPC ............... *G16H 40/40* (2018.01); *G06F 8/60* (2013.01); *G06F 8/65* (2013.01); *G06F 21/57* (2013.01);
(Continued)

(58) Field of Classification Search
CPC .. G16H 40/40; G06F 8/60; G06F 8/65; H04L 9/3239; H04L 9/3263; H04L 2209/26; H04L 2209/88
See application file for complete search history.

(56) References Cited

U.S. PATENT DOCUMENTS 5,855,594 A 1/1999 Olive et al.
6,341,287 B1 1/2002 Sziklai et al.
(Continued)

FOREIGN PATENT DOCUMENTS

WO 2010132617 11/2010

OTHER PUBLICATIONS

"Postmarket Management of Cybersecurity in Medical Devices: Guidance for Industry and Food and Drug Administration Staff", Dec. 28, 2016, U.S. Department of Health and Human Services, Food and Drug Administration, 30 pages.
(Continued)

*Primary Examiner* — Darshan I Dhruv
(74) *Attorney, Agent, or Firm* — Boyle Fredrickson, S.C.

(57) ABSTRACT

In the present invention, a system and method is provided for the self-certification of third party software products for use on medical products by the customer. The system enables the customer to test, qualify, and certify a third party software product for use on a controlled medical device independent of any testing or other intervention by the manufacturer. The system can be located on the particular medical device and provides internal testing and certification mechanisms to promote/authorize third party software products onto to the device/software authorization catalog, as well as notification to the manufacturer of the customer approved addition to the device certified third party software product catalog.

14 Claims, 2 Drawing Sheets

(51) Int. Cl.
*G06F 8/65* (2018.01)
*G16H 40/67* (2018.01)
*G16H 10/60* (2018.01)
*G06F 21/57* (2013.01)
*G06F 8/60* (2018.01)

(52) U.S. Cl.
CPC ............ *G16H 10/60* (2018.01); *G16H 40/67* (2018.01); *H04L 9/3239* (2013.01); *H04L 9/3263* (2013.01); *H04L 2209/26* (2013.01); *H04L 2209/88* (2013.01)

(56) References Cited

U.S. PATENT DOCUMENTS

| | | | |
|---|---|---|---|
| 7,080,356 B2 | 7/2006 | Atallah et al. | |
| 7,099,916 B1* | 8/2006 | Hericourt | H04L 67/06 709/203 |
| 8,090,445 B2 | 1/2012 | Ginggen | |
| 8,521,247 B2 | 8/2013 | Wood | |
| 8,776,238 B2 | 7/2014 | Pomerantz | |
| 9,003,390 B2 | 4/2015 | Moritzen et al. | |
| 2002/0083213 A1* | 6/2002 | Oberstein | G06F 11/3684 719/313 |
| 2004/0044996 A1* | 3/2004 | Atallah | G06F 8/71 717/169 |
| 2004/0054988 A1* | 3/2004 | Atallah | G06F 8/71 717/122 |
| 2007/0172062 A1 | 7/2007 | Waldo et al. | |
| 2008/0262968 A1* | 10/2008 | Saxena | G06F 21/10 705/51 |
| 2009/0100412 A1* | 4/2009 | Weiss | G06F 11/3684 717/124 |
| 2010/0017848 A1* | 1/2010 | Pomerantz | H04L 63/20 726/2 |
| 2010/0292556 A1* | 11/2010 | Golden | G16H 40/40 600/364 |
| 2011/0283260 A1 | 11/2011 | Bucuvalas | |
| 2011/0296395 A1* | 12/2011 | Vidal | G06F 9/44589 717/171 |
| 2012/0137127 A1* | 5/2012 | Jain | H04L 9/3271 713/156 |
| 2012/0137349 A1* | 5/2012 | Lundblade | H04W 12/0023 726/4 |
| 2012/0172687 A1* | 7/2012 | Wood | A61B 5/7246 600/323 |
| 2013/0036412 A1* | 2/2013 | Birtwhistle | G06F 8/65 717/171 |
| 2013/0086573 A1 | 4/2013 | Moritzen et al. | |
| 2013/0283377 A1* | 10/2013 | Das | H04L 63/1441 726/23 |
| 2013/0297973 A1* | 11/2013 | Hyland | G16H 10/60 714/27 |
| 2013/0344906 A1 | 12/2013 | Etemad | |
| 2014/0053145 A1 | 2/2014 | Steigleder | |
| 2015/0089479 A1* | 3/2015 | Chen | G06F 11/3664 717/124 |
| 2015/0356297 A1* | 12/2015 | Guri | G06F 21/566 726/23 |
| 2015/0379221 A1* | 12/2015 | Yeager | G16H 40/63 715/771 |
| 2016/0129185 A1 | 5/2016 | Ludolph | |
| 2017/0060560 A1* | 3/2017 | Kumar | G06F 11/3688 |
| 2017/0195424 A1* | 7/2017 | Nasir | H04L 67/36 |
| 2017/0220782 A1* | 8/2017 | Alsanousi | G06F 21/126 |
| 2017/0302657 A1* | 10/2017 | Moskal | H04L 63/0823 |
| 2017/0319861 A1* | 11/2017 | Golden | G16H 40/40 |
| 2018/0189449 A1* | 7/2018 | Karumba | G16H 40/20 |
| 2018/0189797 A1* | 7/2018 | Ravi | G06F 21/552 |

OTHER PUBLICATIONS

International Search Report and Written Opinion issued in connection with corresponding WO Application No. PCT/US2018/050698, dated Jan. 7, 2019, 12 pages.

* cited by examiner

METHOD AND SYSTEM FOR USER-VERIFIABLE CERTIFICATION OF SOFTWARE FOR MEDICAL DEVICES

BACKGROUND OF INVENTION

The invention relates generally to medical devices or systems which include third party software added to the devices or systems separate from the original software provided by the manufacturer of the devices or systems.

Various medical devices and systems are used in an increasing number of medical procedures to evaluate various conditions of the patient with which the device or system is utilized. Virtually all of these devices currently require software packages to properly operate the device or system during evaluation or monitoring of the patient. Upon initial manufacture, the required software for the proper operation of the device is installed on the device by the manufacturer. The manufacturer can the test the device prior to shipment in order to confirm the proper operation of the device. In addition, upon receipt of the device, the end user, with or without the assistance of the manufacturer, can confirm the proper operation of the device on site after installation.

However, during the useful life of the device, many upgrades or additions to the original manufacturer's operating system/software package are required to address various needs or issues that develop with regard to the original software package. These issues with the original software package can include necessary and/or regular upgrades to the functionality of the software package, or patches to close security concerns discovered within the software package, among others.

While these modifications to the original software are readily accomplished through a variety of direct and indirect mechanisms, managing postmarket cybersecurity vulnerabilities to protect against security breaches in the medical devices has become a significant issue. This significance is magnified by the issue that the modification(s) to the software on the devices is most often done in a reactive manner, where the manufacturer provides patches or other modifications after issues with the original software have arisen.

To address this, and for many other reasons most consumers of the medical devices have developed internal information security measures that are designed to protect the information stored in their systems, including the information obtained from the medical devices. For manufacturers of the devices, difficulty arises in supporting the enormous variance in customer security strategies and corresponding information technology (IT) infrastructure, along with any third party IT solutions employed by the consumer for everything from specialist IT departmental solutions, such as cardiovascular information systems, to general electronic health record systems while simultaneously supporting the requirements of current good manufacturing practices. This requires the manufacturers to test the compatibility of the third party software product(s) and release the revised medical product software to all customers including those that are not interested in use of the third-party software product. Also, the configuration of existing software has to be evaluated with regard to any updates as, for example, certain operating system settings to harden the system may be applied by the customer and lock the system down to a greater degree than originally shipped. This process is further compounded by the requirement in supporting these devices or products in the field to assure timely updates of the device software package relating to these third-party software products that are on completely asynchronous and random upgrade calendars.

In one particular attempt to alleviate these issues, a self-testing method for medical devices is disclosed in U.S. Pat. No. 9,003,390 (the '390 patent), hereby expressly incorporated by reference for all purposes. In the '390 patent, a patch module contained within a medical device receives an operating system software patch provided to the device in order to update the operating system software already present on the device. The patch module performs a self-test upon the installation of the operating system patch in order to confirm the proper installation of the software patch within the operating system of the medical device.

However, while capable of implementing a self-test concerning the integration of a software patch directly to the operating system for the medical device, the method and system disclosed in the '390 patent is significantly limited to only the modification of the operating system, and in particular to the modification of the operating system as a result of installed operating system software patches. Thus, the system and method of the '390 patent excludes a significant portion of software installations to a medical device that include software from a third party source that operates in conjunction with the operating system, and/or which may affect the operation of the operating system but that is not an operating system patch provided by the operating system manufacturer.

Accordingly, it is desirable to develop a system and method for streamlining the certification of third party software products for safe and effective use on a medical device or product without intervention by the device manufacturer.

BRIEF DESCRIPTION OF THE INVENTION

There is a need or desire for a method and system that enables consumers of a medical device to self-certify a third party software product for use on the device. The above-mentioned drawbacks and needs are addressed by the embodiments described herein in the following description.

According to one exemplary aspect of the invention, a system and method is provided for the self-certification of third party software products for use on medical products by the customer. The system enables the customer to test, qualify, and certify a third party software product for use on a controlled medical device independent of any testing or other intervention by the manufacturer. The system can be located on the particular medical device and provides internal testing and certification mechanisms to promote/authorize third party software products onto to the device/software authorization catalog, as well as notification to the manufacturer of the customer approved addition to the device certified third party software product catalog to maintain the device in a enforced and controlled state that is compliant with regulatory concerns.

According to another exemplary embodiment of the invention, the system and method addresses customer integration of controlled medical products and the corresponding strict verification and validation requirements needed to assure safe and effective function of these devices in the medical institution. The need for rapid security deployment, and numerous commercially available security measures to assure security-in-depth creates a tension between the objectives of the safe and effective operation of a medical device, and keeping hostile entities out of complex medical devices and systems. The inventive system and method described herein remedies this situation by allowing customer's IT departments freedom to operate, while preserving the sanctity of the medical device through the deployment of the system that enables both requirements to co-exist. The system and method creates a framework in which the customer can repeat manufacturer third party software product tests on the medical device in order to independently confirm the safe and effective operation of the device with the added third party software product. The system and method also provides safeguards that changes to the device via the third party software products cannot be made to the medical device without performing the necessary assurance actions and/or tests utilizing the system and method. In this way flexibility in deployment is achieved and medical device performance is confirmed.

In one exemplary embodiment of the invention, this system and method provides the technical effect of an in depth analysis of the essential performance of the medical device and an impact analysis of third party software product on this essential performance using the device risk management file stored on the device. The analysis initially identifies the necessary requirement(s) of the test framework to so that the analysis to be performed via the test contains the necessary test scope. Upon completion of the analysis by the system, a successful execution of this test framework provides objective evidence that essential performance of the device and all required software safety mitigations are maintained when the third party software is employed on the device. These test results will be stored as objective evidence on the device and/or system of the certification of the third party software product and a cryptographic secure certificate will be generated by the system. The certificate can then be utilized to unlock the medical device for patient use in conjunction with the certified third party software product. This certification can also be forwarded to the device manufacturer for use in conjunction with additional testing or as an addition to the device risk management files of other devices.

According to another aspect of the invention, a method for certifying a software download, update, installation or configuration change for safe and effective system operation of a medical device at an onsite location for the medical device includes the steps of providing a certification system including an analysis engine configured to conduct a regression analysis on the operating system after integration with the software download and a risk management database operably connected to the analysis engine, the risk analysis database including stored information on a software authorization catalog and essential operational criteria for the medical device, performing the regression analysis and providing an encrypted certificate of compatibility upon successful completion of the regression analysis, wherein the software download, update, installation or configuration change is not an operating system software patch.

According to still another aspect of the invention, a system for certifying the compatibility of a software download, update, installation or configuration change for safe and effective system operation of a medical device with an operating system of a medical device, includes an analysis engine configured to perform a regression analysis on the operating system of the medical device after integration of the software download with the operating system, a risk management database operably connected to the analysis engine and including stored information on a software authorization catalog and essential operational criteria for the medical device, wherein the system is operably connected to a central processing unit of the medical device and wherein the software download, update, installation or configuration change is not an operating system software patch.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
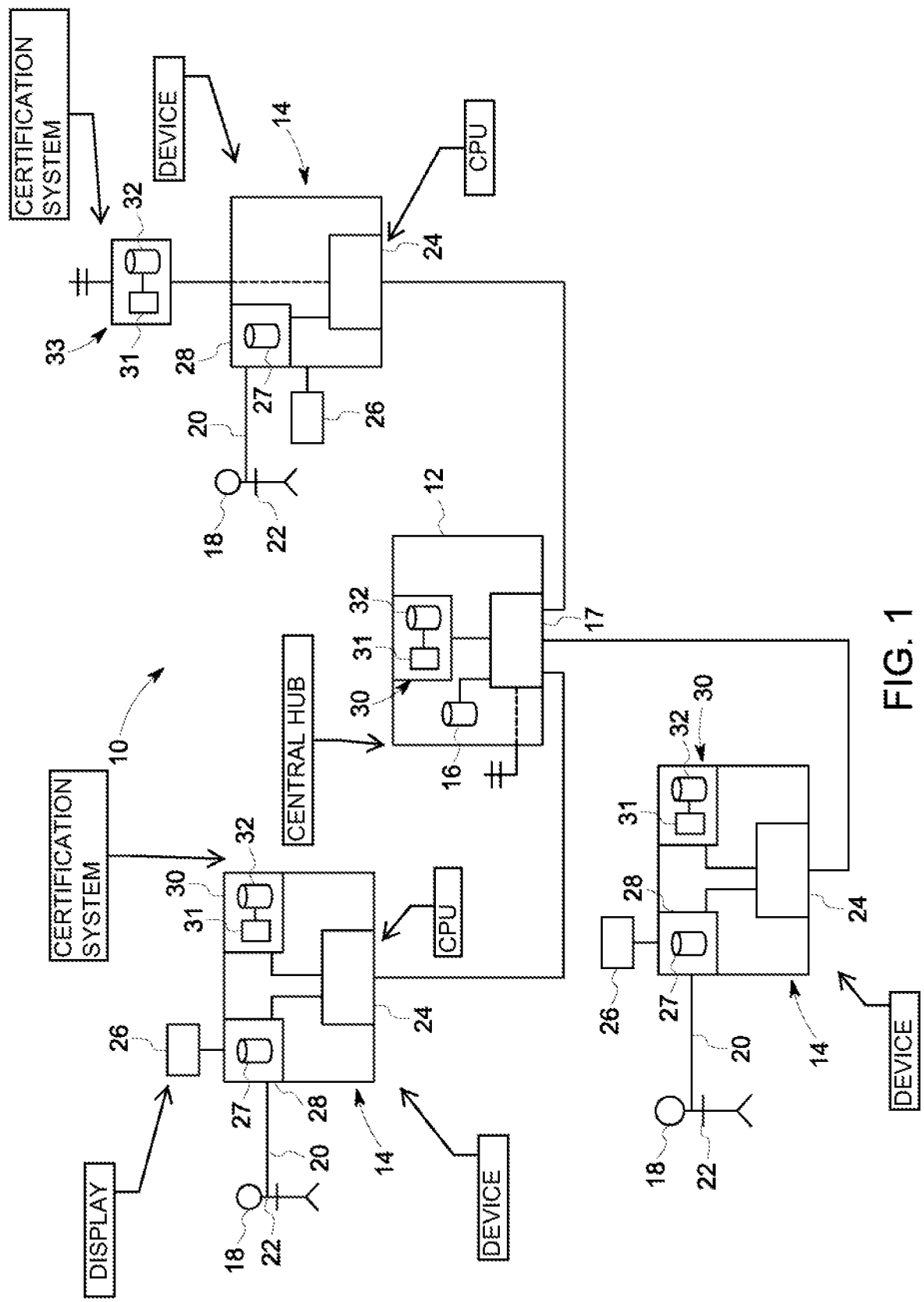
FIG. 1 is a schematic representation of a medical facility network including medical devices having the self-certification system and method according to one exemplary embodiment of the present invention.

FIG. 1 illustrates one exemplary embodiment of a medical device network 10 such as is utilized in a hospital or other medical care facility. The network 10 includes a central unit 12 to which a number of individual medical devices 14 are connected using a wired or wireless connection. The central unit 12 functions as a central hub for the patient information obtained by the individual medical devices 14 and can be operated to monitor the patient information from a single location. The central hub 12 can additionally include a database 16 for storage of the patient information and a central processing unit (CPU) 17 for analyzing the patient information in database 16 and for transmitting the patient information to various other locations or devices (not shown).

With regard to the medical devices 14, the devices 14 can be any suitable type of patient monitoring or treatment device, such as an electrophysiology recording and/or mapping system, among others. The devices 14 are engaged with the patient 18 via leads 20 connected to the device 14 at one end and to one or more sensors or treatment electrodes 22 disposed on or within the patient 18 at the opposite end. The information obtained from the sensor(s) 22 is received by the devices 14 via the leads 20 and can be analyzed by a central processing unit (CPU) 24 disposed within the device 14 for illustration on a display 26 for the device 14.

For the proper operation of the device 14, the CPU 24 includes a set(s) of instructions/operating system 27 in the form of software stored on the device 14 within a database 28 operably connected to the CPU 24. This software 27 is originally placed on the device 14 within the database 28 by the original manufacturer of the device 14 and tested to ensure proper operation of the device 14 for its intended purpose.

On many occasions, due to the requirements of the particular network 10 within which the device 14 is to be placed, the operating software 27 within the database 28 must be modified through the use of different upgrades or other manufacturer-developed or third party software packages in order to be rendered compatible with the operating system for the network 10 stored in the central hub 12. These modifications or upgrades must be compatible with the original software in the database 28 in order to maintain the proper operation of the device 14.

In order to determine the compatibility of the alterations or upgrades with the original operating system 27 in the database 28 of the device 14, the device 14 includes a certification system 30. The certification system 30 can be formed as a part of the device 14, or in alternative exemplary embodiments can be employed as a separate device 33 is operably connectable to the device 14 in order to provide the certification function, or can be stored on the central hub 12 of the network 10 in order to be triggered and/or accessed by the download of a software upgrade onto a particular device 14. In other exemplary embodiments, of the invention, the certification system 30 can be isolated from the production operating system 27. It would contain production equivalent hardware and would connect to a calibrated simulator system/analysis engine 31 instead of to the patient 18. The certification system 30 can also contain a test framework (not shown) stored within the system 30 to provide the capability of the system 30 to execute the required testing, either automatically or as a result of manual intervention/authorization. The system 30 can also be configured to accommodate additional instrumentation on the device 14, which also deepens visibility/accessibility into the underlying operation of the device 14/operating system 27 so that a more sophisticated functional analysis can be performed than would be possible on a production configuration. Additionally, in another exemplary embodiment the entire certification system 30 could be located off-site and the testing could be handled by an authorized 3rd party or at a remote central location in a large hospital chain.

The certification system 30 operates an analysis engine/central processing unit 31 operably contained within the system 30 to employ a suitable analysis, such as a regression suite/testing procedure on the operating system 27 of the device 14 when an upgrade has been downloaded onto the device 14. The certification system 30 in one exemplary embodiment employs a test framework and a suite of targeted regression tests for use by the analysis engine 31 that is stored in the system 30, such as in risk management database 32. These regression tests could be executed via an automated test harness such at "TestComplete" or "HP UFT". The system 30 may also include a manual framework where a human could execute and record results of a test procedure that is not automated. In any suitable process for performing the analysis, the certification system 30 reviews and/or scans the system environment of the device 14 after the download of the upgrade in order to detect any changes made in an of the essential operational criteria for the operating system 27 of the device 14. The system environment of the device 14 can be configured as desired, and can include, but is no limited to the security settings, executables and registry settings, among other system environment variables. The scan by the certification system 30 looks for changes in the system environment and whether these changes affect any essential operation criteria of the device 14. The essential operational criteria are necessary functions for the proper operation of the device 14 and in one exemplary embodiment are configured/stored within a risk management database 32 within the device 14 that is operably connected to be accessible by the certification system 30. The risk management database 32 also includes information concerning manufacturer-authorized third party software packages for use with the device 14, and the objective testing evidence and authorization certificates created as a result of prior testing performed by the certification system 30. The information stored in the risk management database 32 is employed by the certification system 30 prior to any modification to the device 14 in order to enable the certification system 30 to maintain these essential performance criteria throughout all software downloads and/or upgrades performed on the device 14.

With the certification system 30, the device 14 is able to provide objective evidence of safe and effective product design and follow of design controls throughout the useful life of the device 14 that conform to various administrative requirements, such as from the Food and Drug Administration (FDA) requirements, including those documented in the FDA Guidance entitled: *Postmarket Management of Cybersecurity in Medical Devices—Guidance for Industry and Food and Drug Administration Staff*, Document No. 1400044, which is expressly incorporated herein by reference for all purposes, and other international regulatory bodies. The certification system 30 enables verification of the device 14 and in particular the verification of the operating software 27 of the device 14 using an automated test environment, with test scripts in the certification system 30 that can execute device 14 functionality, confirm correct execution and automatically record the results in a computer readable format, as is currently done manually by a dedicated test engineer. The certification system 30 is repeatable, and easily and automatically executable without the specialist skills, rigor and training of a dedicated test engineer, such that the certification system 30 can be readily employed for integration testing of a device 14 using the certification system 30 to ensure that the medical operational characteristic/essential operational criteria of the device 14 can be tested to conform the manufacturers original results. Further, the certification system 30 can be utilized with third party software packages and/or downloads from various security vendors, such as Norton®, McAfee®, Trend®, and others, or third party medical software packages, such as various electronic health records systems available from Cerner®, EPIC®, and MedTech®, among others, the certification system 30 can check the safe and effect function of the medical device 14 when used in the presence of these third-party software packages.

The issue addressed by the certificate system 30 is that the customer creates a device 14 that differs from what the manufacturer originally provided upon the download and application on of any third party software package onto the device 14. While the certification system 30 tests and provides objective evidence of the functioning of the device 14 in conjunction with the third party software, use of the certification system 30 also provides a method to control and manage the change to the medical device 14 that the customer intends to permit. The original medical device 14 is developed with a permitted "software catalog" in database 28 that stores and/or records all permitted safe third party software packages, e.g., not operating system software patches, installed and/or approved by the device manufacturer for use on the device 14. The certification system 30 enables the consumer/customer of the medical device 14 to perform on site testing that can modify the approved software catalog for the device 14 to self-certify new software packages and/or upgrades for use with the device 14. In addition, upon successful completion of the testing by the certification system 30, the system 30 provides the customer with a "certificate" or and "customer certified acceptance test" (CCAT) that includes details about the software package that was tested and test results, including the manufacturer, software product name, version number, and test history. Once created by the certification system 30, the certificate/CCAT is subsequently stored in the risk management database 32 and provided to the customer and required to be input into the medical device 14 prior to deployment of the third-party software package for verification purposes, as no software can be installed on the medical device 14 without this certification process being completed by the certification system 30.

Figure 2:
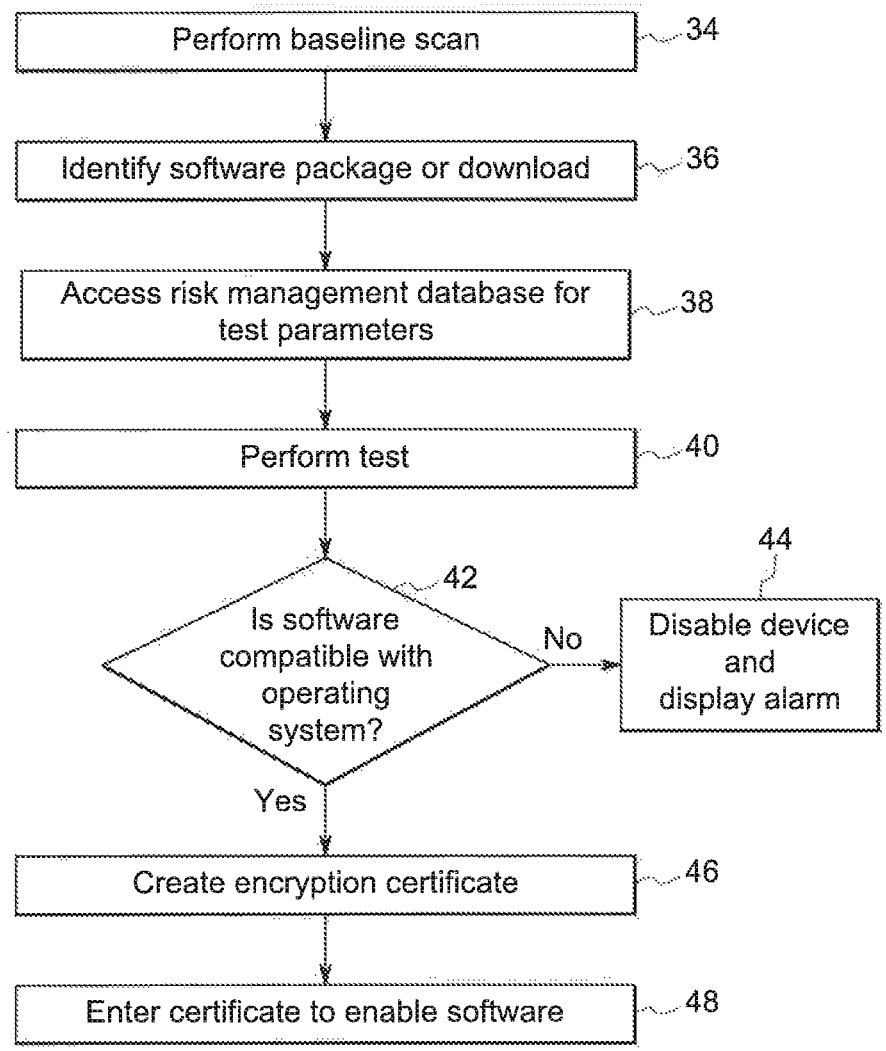
FIG. 2 is a schematic representation of a method of operation of the system of FIG. 1 according to an exemplary embodiment of the invention.

In operation, referring now to FIG. 2, in block 34 as an optional first step the certification system 30 can be operated with or connected to the device 14 in order to perform and obtain a baseline scan of the system environment of the device 14 as provided by the manufacturer for utilization on later tests run by the certification system 30.

In block 36, initially the software package to be utilized with the device 14 is identified with the certification system 30. This can be accomplished by downloading the software onto the certification system 30 itself where the system 30 constitutes a device separate from the medical device 14, downloading the software directly onto the device 14 in a safe mode under the control of the certification system 30 on the device 14, or by downloading the software onto the central hub 12 of the network 10 to be accessed by the certification system 30, among other suitable manners. Then, in block 38, the certification system 30 accesses the risk management database 32 to determine the test framework and/or protocols for the analysis to be performed by the certification system 30 in view of the attributes of the software to be tested. In one exemplary embodiment, the protocols for the analysis performed by the certification system 30 are determined through a process called impact analysis. In this process, the modified parts of the software system 27 are linked back to medical device requirement through a trace analysis report that is part of the device creation. This report provides a mapping from "risk analysis file→software item→medical device requirement→test procedure which demonstrates that requirement is met". So in an exemplary embodiment, the mapping for the protocol is provided in the device 14 and system 30 prior to original shipping of the product/device 14. When an update or new software package is received onto the device 14, the system 30 analyses what is changed by the update/new software and follow the mapping to decide which tests to run. In other exemplary embodiments, the system 30 can determine what parts of the operating system 27 have changed and then can determine what aspects of the operating system 27 might be affected by that change and correspondingly what tests cover that effect(s) to run the appropriate tests. Once determined, the certification system 30 proceed in block 40 to perform the test/regression analysis on the downloaded software package.

In performing the test, the certification system 30 will determine if the downloaded package or software has any effect on the system environment for the device 14, including the essential performance criteria and/or safety characteristics affecting the safe and effective operation of the device 14, as compared to the original or prior system environment as determined from the initial scan of the original system environment in block 34. Based on the protocols provided for the test, the certification system 30 can additionally attempt to minimize and/or eliminate any of these changes created by the downloaded software depending upon a level of authorization for these changes provided to or selected by the customer for the certification system 30, and employed in terms of the trace analysis mapping by determining the minimum set of changes which produces the smallest number of end test cases linked through the mapping.

In one exemplary embodiment of the invention, the impact analysis employs one or more lists to scan the operating system 27 of the PC/CPU/device 14 for changes resulting from a third party software download, update, installation or configuration change of the operating system 27. The lists are used to ensure that a hard drive image process creates the proper responses and thus is used as one of the inputs to the analysis engine 31. There is a lot of different information that could be contained in the lists utilized in the impact analysis. Without being limiting, some exemplary lists that can be employed for use in the impact analysis include one or more of the following:

List(s) of hashes of the PC and hardware card BIOS
List(s) of drivers installed and their versions information
List(s) of all security groups
List(s) of all users
List(s) of member(s) of each computer security group
List(s) of hashes of all system files
List(s) of hashes of program executables installed
List(s) of all hidden files
List(s) of all network firewall rules
List(s) of all network configurations
List(s) of all security policies
List(s) of shared folders These lists are generated during/in an initial install when the configuration is known good and then re-generated and compared to determine areas of change that may require testing In performing the impact analysis, the analysis engine 31 processes that list(s) and creates a list of "suspect" categories that have scan results different from the last approved state for the operating system 27. Each of these suspects would then be processed by mapping that category to associated product requirements, for example, the computer users and groups analysis category would relate to a set of product security requirements. The analysis engine 31 can then follow these requirements down to the specific tests associated with a provided trace matrix for those requirements. Thus the analysis engine 31, in performing the impact analysis, performs the initial scan of changes to the operating system 27 made by the software package, produces a list of suspects as a result of the changes determined in the initial scan, determines a set of test procedures/trace matrix associated with required product/operating system attributes, and launches the test engine to perform those procedures. If the result of the test procedure/trace matrix is the "expected result" then the test passes, and if all tests pass then the certificate of compliance is generated and certificate and scan results are distrusted to all systems as they now represent a new "known good" or baseline state for the operating system 27.

If, as a result of the test, if in decision block 42 the certification system 30 determines that critical incompatibilities exist with regard to the downloaded software package and the original and/or stored system environment, thereby compromising the safe and effective operation of the device 14, the system 30 will provide this information, such as in the form of an alarm, to the customer in block 44, and will prevent operation of the medical device 14 with the software However, if the certification system 30 determines there are no incompatibilities between the downloaded software package and the original and/or stored system environment, or that any changes to the original and/or stored system environment are not relevant to the operation of the device 14 and/or are mitigated by the certification system 30, the system 30 proceeds to block 46 and creates a certificate for the authorization of the use of the downloaded software package with the device 14. In an exemplary embodiment of the invention, the certificate is an encryption-style certificate including information specific to the software package tested that is stored on the device 14 and/or on the network 10 connected to the device 14, and is provided to the customer as an output from the certification system 30 in digital form and/or physical form, e.g., paper. This certificate is subsequently required to be entered into the device 14 and confirmed by the comparison with the copy of the certificate stored in the device 14 in order to enable the software package that is the subject of the certificate to be downloaded and operated on the device 14. In certain exemplary embodiments, the information provided on the certificate can include certain warnings regarding changes to the overall system environment and/or essential operational criteria made by the software package/download and detected by the certification system 30 that were determined not to be incompatible with the operation of the device 14, but that could present issues if the software relating to the certificate is employed on the device 14.

In conjunction with the creation of the certificate, the certification system 30 can additionally update the information in the risk management database 32, including the authorization catalog and the certificate listing to include the information regarding the tested software package. The results of the testing of the software package are also stored within the database, e.g., in association with the certificate for the third party software package tested, in order to provide a record of the objective evidence of the certification of the software package for later verification purposes, if necessary. Further, in other exemplary embodiments, the certification system 30 can provide the results of the test to the manufacturer of the device 14, such as through a wireless or Internet connection via the network 10, to enable the manufacturer to review the test results and potentially update the authorization catalog on subsequently manufactured devices 14.

After providing the certificate to the customer in block 46, the customer can then enter the certificate and/or the information contained on the certificate into the device 14 in order to enable the download and operation of the software that was the subject of the test on the device 14. In this manner the certification system 30 enables the customer to test on site the compatibility of third party software packages with the overall system environment of the device 14. In various exemplary embodiments of the invention, the testing done by the certification system 30 can be initiated automatically, such as on initial start or boot up of the device 14, or manually by the customer.

The certification system 30 also provides a number of technical advantages, including but not limited to:

1. enabling customer-driven certification of third party software products used on a medical device 14;
2. enabling certification through repetition of manufacturer core testing by the certification system 30 without the need for direct customer interaction;
3. automating the testing, collection of data, and certification for third party software;
4. preventing inappropriate use of the device 14 by simply installing untested, and unapproved third party software inventory onto the medical device 14; and
5. notifying the manufacturer of change in configuration, and customer acceptance of the system environment of a device 14 through an on site, automated certification process.

The certification system 30 also provides certain commercial advantages, including but not limited to:

1. enabling customer choices on their institution security policies as related to the system environment of the device 14 covered by those policies;
2. enabling customer choice on security measures and investments as related to the system environment of the device 14 covered by those security measures;
3. enabling customer integration of third party IT software products on the medical device 14;
4. enabling clear accountability on decisions made, and preventing deployment of software that negatively effects the medical device 14 performance;
5. establishing breakthrough product functionality that is distinguished in the market place; and
6. providing an onsite, customer operable certification system as a chargeable, revenue bearing functionality for the medical device 14.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for certifying a software download, update, installation or configuration change for safe and effective system operation of a medical monitoring or treatment device at an onsite location for the medical monitoring or treatment device comprising the steps of:
   providing a certification system on the medical monitoring or treatment device;
   the certification system including an analysis engine configured to conduct a regression analysis on an operating system for the medical monitoring or treatment device after integration with the software download and a risk management database operably connected to the analysis engine, the risk management database including stored information on a software authorization catalog and essential operational criteria for the medical monitoring or treatment device;
   performing the regression analysis;
   providing a user with an encrypted certificate of compatibility upon successful completion of the regression analysis, wherein the encrypted certificate includes warnings regarding changes to the operating system made by the software download, update, installation or configuration change, and wherein the software download, update, installation or configuration change is not an operating system software patch;
   storing a copy of the encrypted certificate on the medical monitoring or treatment device; and comparing the encrypted certificate provided to the user with a copy of the encrypted certificate stored on the medical monitoring or treatment device, wherein the step of performing the regression analysis comprises determining a testing protocol for the regression analysis with information from the risk management database, and wherein the step of comparing the encrypted certificate comprises the user entering the encrypted certificate into the medical monitoring or treatment device for comparison with the stored copy to enable operation of the software download with the operating system.

2. The method of claim 1 further comprising the step of identifying the software download with the certification system prior to conducting the regression analysis.

3. The method of claim 2 wherein the step of identifying the software download comprises downloading the software into the certification system.

4. The method of claim 1 wherein the step of determining the testing protocol comprises selecting essential operating criteria from the risk management database.

5. The method of claim 1 wherein the step of determining the testing protocol comprises enabling modification of the operating system by the certification system during the regression analysis to minimize changes to the operating system by the software download.

6. The method of claim 1 further comprising the step of storing test results for the software download in the risk management database upon successful completion of the regression analysis.

7. The method of claim 1 further comprising the step of outputting information regarding changes made to the operating system by the certification system.

8. The method of claim 7 wherein the information output includes a warning regarding the changes made to the operating system.

9. The method of claim 1 further comprising the step of updating a software authorization catalog in the risk management database with information on the software download.

10. The method of claim 1 further comprising the step of forwarding information on the test results upon successful completion of regression analysis.

11. The method of claim 1 wherein the step of performing the regression comprises initiating the regression analysis by downloading the software onto the medical monitoring or treatment device.

12. The method of claim 1 wherein the step of performing the regression comprises initiating the regression analysis by downloading the software onto a network connected to the medical monitoring or treatment device.

13. The method of claim 1 wherein the step of providing the certification system comprises downloading the certification system onto the medical device.

14. A system for certifying compatibility of a software download, update, installation or configuration change for safe and effective system operation of a medical monitoring or treatment device with an operating system of the medical monitoring or treatment device, the system comprising:

an analysis engine located within the medical monitoring or treatment device and configured to perform a regression analysis on the operating system of the medical monitoring or treatment device after integration of the software download with the operating system;

an electronic memory unit including a risk management database operably connected to the analysis engine and including stored information on a software authorization catalog and essential operational criteria for the medical monitoring or treatment device and a stored encrypted certificate to be compared with an entered encrypted certificate provided by the analysis engine to a user and subsequently entered into the medical monitoring or treatment device by the user to enable operation of the software download on the medical monitoring or treatment device, wherein the system is operably connected to a central processing unit of the medical monitoring or treatment device and wherein the regression analysis performed comprises determining a testing protocol for the regression analysis with information from the risk management database.

\* \* \* \* \*